United States Patent [19]

Horrobin et al.

[11] Patent Number: 5,922,345
[45] Date of Patent: *Jul. 13, 1999

[54] NUTRITION

[75] Inventors: David F. Horrobin, Surrey, United Kingdom; Lars Lindmark, Falsterbo, Sweden

[73] Assignee: Scotia Holdings Plc, United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/584,426

[22] Filed: Jan. 11, 1996

Related U.S. Application Data

[63] Continuation-in-part of application No. 08/405,431, Mar. 16, 1995., abandoned, which is a continuation of application No. 08/208,481, Mar. 8, 1994., abandoned, which is a continuation of application No. 07/802,644, Dec. 9, 1991., abandoned

[30] Foreign Application Priority Data

Dec. 7, 1990 [GB] United Kingdom .................. 9026648

[51] Int. Cl.⁶ .................................................. A61K 31/23
[52] U.S. Cl. ........................ 424/439; 514/558; 514/560
[58] Field of Search ..................... 514/558, 560; 424/439

[56] References Cited

U.S. PATENT DOCUMENTS

| | | | |
|---|---|---|---|
| 4,668,704 | 5/1987 | Hollander | 514/560 |
| 4,703,060 | 10/1987 | Traitler | 514/549 |
| 4,752,618 | 6/1988 | Mascioli | 514/560 |
| 4,906,664 | 3/1990 | Bistrian | 514/552 |
| 5,039,704 | 8/1991 | Smith | 514/563 |
| 5,053,387 | 10/1991 | Alexander | 514/561 |

FOREIGN PATENT DOCUMENTS

| | | |
|---|---|---|
| B-30577/84 | 1/1985 | Australia . |
| 0132089 | 1/1985 | European Pat. Off. . |
| 0 311 091 | 4/1989 | European Pat. Off. . |
| 0 347 056 | 12/1989 | European Pat. Off. . |
| 37 21 137 | 1/1989 | Germany . |
| A-56 122 312 | 9/1981 | Japan . |
| A-60 169418 | 2/1985 | Japan . |
| 0169418 | 9/1985 | Japan . |
| 0248610 | 12/1985 | Japan . |
| 187908 | 5/1984 | New Zealand . |
| 88/02221 | 4/1983 | WIPO . |
| WO-A 8 809 325 | 1/1988 | WIPO . |
| 88/01861 | 3/1988 | WIPO . |

OTHER PUBLICATIONS

WPIL Abstract No. 85–253800, Derwent Publications Ltd, London, GB; and JP–A–60 169 418 (Nippon Oils & Fats).
WPIL Abstract No. 88–353913, Derwent Publications Ltd, London, GB; and WO–A–8 809 325 (Nisshin Oil Mills et al).
WPIL Abstract No. 81–82494D, Derwent Publications Ltd, London, GB; and JP–A–56 122 312 (Kagakuhin Kensa Kyo).
Derwent 85/253800 [41]JP840025184 840215.
Johnson, Gastroenterology 68 pp. 1173–1183, 1975.
Pathophysiology Clinical Concepts of Disease Processes. Ed. by Anderson et al, McGraw–Hill Book Company, pp. 388–389, 887–893, 1986.

*Primary Examiner*—Gollamudi S. Kishore
*Attorney, Agent, or Firm*—Nixon & Vanderhye

[57] ABSTRACT

Countering side effects of parenteral or fluid-diet enteral nutrition by adding one or more 6-desaturated essential fatty acids (EFAs) to parenteral or enteral composition (particularly low-fat compositions) being given, or giving them in addition to the compositions.

3 Claims, 1 Drawing Sheet

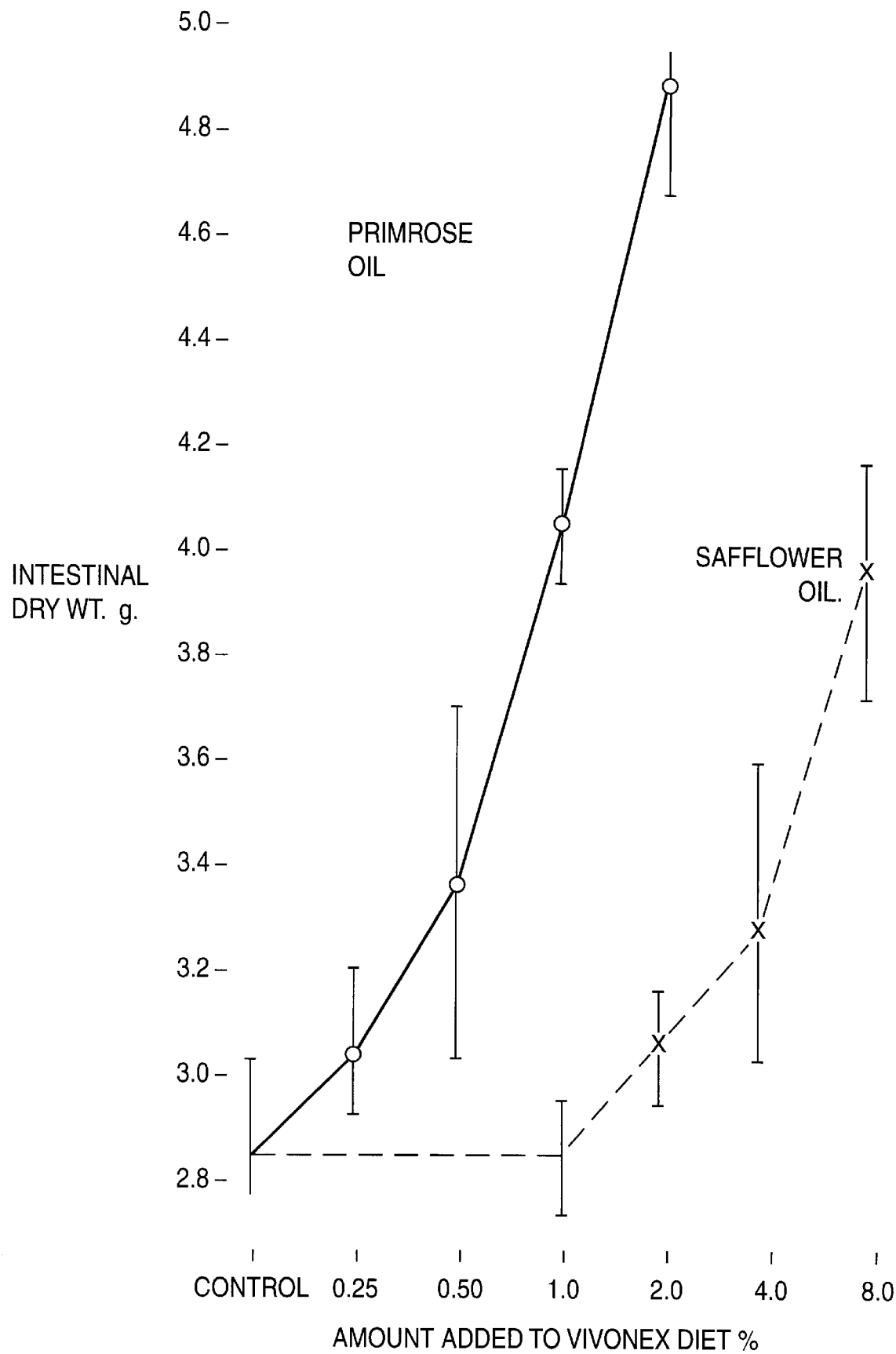

NUTRITION

This application is a continuation-in-part of application Ser. No. 08/405,431, filed Mar. 16, 1995 which is a continuation of Ser. No. 08/208,481 filed Mar. 8, 1994 which is a continuation of Ser. No. 07/802,644 filed Dec. 19, 1991 all now abandoned.

FIELD OF THE INVENTION

The invention relates to nutrition and in particular to countering side effects of parenteral or fluid-diet enteral nutrition.

GENERAL BACKGROUND

There are increasing numbers of patients who are being fed completely via parenteral fluids for short and long periods of time. The most obvious examples are patients undergoing post-operative care. But there are also many patients who for various reasons cannot take a diet of normal food and are fed enterally with defined enteral preparations, often containing relatively low levels of fat in general or essential fatty acids (EFAs) in particular (e.g. M. Pettei et al, "Essential fatty acid deficiency with the use of chemically-defined diets", Gastroenterology 1989; 96:A391).

A number of complications can develop in these patients. The include intestinal atrophy, biliary abnormalities, insulin resistance, accumulation of fat in the liver, abnormal activation of the reticulo-endothelial system (particularly with parenteral lipids), abnormal lipoprotein levels and increased protein catabolism. This invention addresses these issues and three of them in particular all of which can occur with both enteral and parenteral artificial nutrition regimes.

(1) There is relatively rapid atrophy of the small intestine and of the villi protruding into the lumen. The villi are the small finger like processes of the intestinal mucosa which project into the intestinal lumen and which are important in increasing the surface area available for the absorption of intestinal contents. As a result, absorption of foods becomes inefficient and when patients start taking normal oral food they cannot utilise it properly. They develop many adverse symptoms such as gastrointestinal motility disburbances, including diarrhoea, pain and malabsorption.

(2) There is rapid accumulation of fine precipitated material (sludge) in bile. This makes the bile thick and viscous and leads to a high risk of developing gall stones.

(3) There can be severe accumulation of fat in the liver, causing fatty liver which may disrupt both the structure and function of the liver.

BACKGROUND OF INVENTION

We have seen that these abnormalities relate to a lack of essential fatty acids of the n-6 and the n-3 series. The main dietary EFAs are linoleic acid (LA) in the n-6 series and alpha-linolenic acid (ALA) in the n-3 series, and the usual fluids for parenteral and enteral nutrition contain only these main dietary EFAs. However, in order to be fully utilised by the body, LA and ALA must first be 6-desaturated and then converted to further metabolites (shown in Table 2 later herein). The products of the 6-desaturation and the further fatty acids arising from them are known as "6-desaturated" EFAs, a term that is convenient though loose. It is these 6-desaturated EFAs which perform many of the functions usually attributed to EFAs overall. Since 6-desaturation is slow and may be impaired by glucose which is found in many enteral and parenteral solutions, those receiving enteral and parenteral nutrition develop deficits of the 6-desaturated EFAs. These deficits can be corrected effectively not by giving LA or ALA but by by-passing the blocked step and providing EFAs such as gamma-linolenic acid (GLA) or dihomo-gamma-linolenic acid (DGLA) of the n-6 series or stearidonic acid, eicosapentaenoic acid (EPA) or docosapentaenoic acid (DHA) of the n-3 series.

We have shown experimentally that intestinal atrophy and fatty liver occur in animals fed a diet commonly used for enteral nutrition ("Vivonex", a trade name, of Norwich Eaton). Rats fed on this diet as their only source of food developed marked loss of intestinal weight, atrophy of the villi and loss of goblet cells from the villi (goblet cells produce mucus and abundant goblet cells are signs of healthy villi) and marked accumulation of fat in the liver. This is surprising because the diet contains approximately 0.7% of its calories in the form of LA. It is usually stated in the literature that 1% of the calories supplied as LA should be sufficient to fulfil the EFA needs of both animals and humans.

BRIEF DESCRIPTION OF THE DRAWING

FIG. 1 is a graph showing the effects on intestinal growth am measured by intestinal weight, of increasing amounts of primrose oil (containing gamma- linolenic acid as the active) and of safflower oil added to an animal's diet.

DESCRIPTION OF THE INVENTION

It is well established that increasing the fat content of the food can stimulate small intestinal growth as indicated by intestinal weight but there are no previous data describing fat effects on the villi and goblet cells. For example, in animals fed the above diet massive replacement of 50% of the calories with evening primrose oil increased intestinal weight. It has been assumed that this effect occurs in response to the simple presence of fat in the intestine and there have been no suggestions that this might be a specific effect of GLA. (A. P. Jenkins et al. "Trophic effect of Efamol evening primrose oil on the rat small intestinal mucosa", Clinical Sci 1989; 77:555–9).

However, we have established that the effect is much more specific to GLA, and that GLA at relatively low levels is exceptionally potent in stimulating small intestine growth. We conducted two experiments.

In one experiment we took nine groups of four rats each. All were fed with the diet. Four of the groups were fed with increasing amounts of evening primrose oil (0.25, 0.5, 1.0 and 2.0% of the diet by weight). Another four groups were fed with increasing amounts of safflower oil (1.0, 2.0, 4.0 and 8.0% of the diet by weight. Preliminary experiments had suggested that 0.25 to 0.5% of evening primrose oil and 1 to 2% of safflower oil were required to produce an effect. At the end of the experiment the rats were killed (four weeks on treatment) and the small intestine was removed, dried and weighed.

The results are shown in the graph herewith.

A clear effect is observed at 0.5% evening primrose oil added to the diet (about 0.04% GLA by weight in the diet), but the effect is still increasing at 2% evening primrose oil in the diet (about 0.16% by weight GLA in the diet). Amounts of GLA in the diet of 0.5 to 1.0% were optimal.

The only difference between safflower oil and evening primrose oil is the content of GLA. Safflower oil contains about 83% of LA, whereas evening primrose oil contains about 73% of LA and 8% of GLA. Yet the two oils had very strikingly different effects on intestinal function. About eight times as much safflower oil as primrose oil was required to produce the same effect. Since primrose oil is only about 8% GLA, this means that GLA as a stimulator of intestinal growth is sixty to eighty times more effective than LA.

These findings were reinforced by a second experiment in which three groups of rats were given the diet, either without fat supplementation or with 2% by weight evening primrose oil or safflower oil. The animals were fed for two weeks and then sacrificed. This time the intestinal wall and the liver were carefully prepared for histological examination. There were four animals in each group. In each animal the lengths of ten villi and the number of goblet cells in each villus were counted. In addition, the liver was stained for fat and examined histologically for fat infiltration. This was scored from 0 to 4 according to the amount of fat present. The results are shown in Table 1 below and, as can be seen, while safflower oil had an undoubted effect in supporting the health of the villi, the evening primrose oil, containing GLA, was far more effective. Similarly, while safflower oil had a weak effect in preventing fatty infiltration, evening primrose oil had a much stronger effect. As far as we are aware this effect on infiltration of fat into the liver is entirely newly discovered. The Table shows changes in rats fed with "Vivonex", "Vivonex" plus 2% safflower oil and "Vivonex" plus 2% evening primrose oil and is as follows:

TABLE 1

|  | "Vivonex" | "Vivonex" + safflower oil | "Vivonex" + evening primrose oil |
|---|---|---|---|
| Weight of intestine (g) | 3.9 ± 0.2 | 3.4 ± 0.4 * | 4.4 ± 0.2 **a |
| Length of villus (distil) ($\mu$m) | 2.0 ± 0.7 | 4.2 ± 0.9 ** | 8.7 ± 1.4 **a |
| No. of goblet cells per villus | 1.0 ± 1.0 | 4.0 ± 1.0 ** | 11.0 ± 3.0 **a |
| Width of muscularis mucosa ($\mu$m) | 3.1 ± 1.0 | 4.4 ± 1.0 ** | 5.2 ± 0.7 ** |
| Mean fatty liver score | 4.0 | 3.3 | 1.0 b |

* Significant at $p<0.05$ as compared to "Vivonex" fed ad lib as sole diet (Student's t test).
** Significant at $p<0.01$ as compared to "Vivonex" fed ad lib as sole diet (Student's t test).
a Significantly different from the safflower oil group at $p<0.01$ (Student's t test).
b Significantly different from both the Vivonex alone and safflower oil groups at $p<0.01$ (Mann-Whitney test).

Although in our experiments the GLA was provided orally, GLA applied parenterally is also effective. This is because EFAs are secreted in the bile and much of the EFA content of the small intestine comes from the bile (M. L. Garg et al, "Intestinal microsomes: poly-unsaturated fatty acid metabolism and regulation of enterocyte transport properties", Canad J. Physiol. Pharmacol 68:636–41, 1990). Further, GLA in the body is rapidly elongated to the next EFA in the chain, DGLA and DGLA is therefore just as effective as GLA.

THE INVENTION

The invention may be broadly stated as countering side effects of parenteral or fluid-diet enteral nutrition characterized by adding one or more 6-desaturated essential fatty acids (EFAs) to the parenteral or enteral composition (particularly low-fat composition) being given, or giving them in addition to the composition, preferably in amounts to provide 0.1 to 1000 mg/kg body weight/day of the 6-desaturated acids, preferably 1 mg to 100 mg/kg/day and very preferably 10 mg to 40 mg/kg/day. The invention includes application of the EFAs by the enteral route or by the parenteral route or simultaneously by both routes. In particular it includes the preparation of sterile ampoules or other preparations containing appropriate amounts of the EFAs which can be added to enteral or parenteral formulations.

The invention further extends to a method of preparation of a medicament for countering such side effects, characterised by preparing the 6-desaturated acids alone or in a dietarily acceptable diluent or carrier to constitute the medicament, either separately from or actually as the parenteral or enteral composition itself.

Illustrative aspects of the invention and background are now discussed, without limitation of its breadth.

The invention still further extends to an additive which can be used to fortify any enteral or parenteral feed, that additive to contain 6-desaturated EFAs of either the n-3 or the n-6 class. Incorporating the desaturated EFAs into enteral or parenteral feeds has been considered but that means that the whole formulation has to be changed. The concept of the additive means that existing formulations which are in use can be modified at the time of use without needing to change the basic formulation. This concept of the additive does not need to be linked only to the prevention of complications, only the general one of nutrition. In this respect the invention gives a method of preparing a medicament by preparing sterile ampoules or other presentations containing 6-desaturated EFAs of the n-6 series, the n-3 series or both and more particularly GLA or DGLA, used to add to fluids for parenteral or enteral nutrition, such presentations to contain sufficient of the EFAs to provide 0.1–1000 mg/kg body weight/day of the or each acid, preferably 1 mg to 100 mg and very preferably 10 mg to 40 mg thereof.

Intestinal Abnormalities, Fatty Infiltration of the Liver

In regard to these aspects within the above broad statement, the invention may be considered as:

1. A method of preventing or reversing intestinal atrophy or fatty infiltration of the liver, in patients undergoing parenteral nutrition or enteral nutrition with artificial fluids, by adding 6-desaturated EFAs of the n-6 series and more particularly GLA or DGLA to the parenteral or enteral fluid, preferably in amounts in the range of 0.01 to 20% of the dry weight of the enteral feed, more preferably 0.5 to 10% and very preferably 0.5 to 2.0%.

2. Such method in which EFAs of the n-3 series are also used, preferably of the kind and preferably also in the amounts specified in relation to biliary abnormalities below.

3. A method of preventing or reversing intestinal atrophy or fatty infiltration of the liver, in patients undergoing parenteral nutrition by applying enterally 6-desaturated EFAs of the n-6 series, more particularly GLA or DGLA in amounts preferably 0.05 to 30 g per day, more preferably 0.5 to 10 g per day and very preferably 1 to 3 g per day.

4. Such method in which EFAs of the n-3 series are also used, preferably of the kind and preferably also in the amounts specified in relation to biliary abnormalities below.

5. A method of preparing a medicament for prevention or reversal of intestinal atrophy or fatty infiltration of the liver, by preparing sterile ampoules or other presentations containing 6-desaturated EFAs of the n-6 series and more particularly GLA or DGLA, used to add to fluids for enteral or parenteral nutrition, or given separately, so providing the necessary n-6 series EFAs for maintenance of small intestine function. Such presentations should desirably contain sufficient n-6 series EFAs to provide 0.1 to 1000 mg/kg/day, preferably 1 mg to 100 mg/kg/day and very preferably 10 mg to 40 mg/kg/day thereof.

6. Such method in which EFAs of the n-3 series are also used, preferably of the kind and preferably also in the amounts specified in relation to biliary abnormalities below.

Biliary Abnormalities

The second major complication of parenteral and enteral nutrition is the high risk of the development of biliary abnormalities and gall stones. The risk is similar to the high risk of gall stones which occurs in animals on a diet deficient in essential fatty acids. Since patients on enteral and parenteral nutrition regimes frequently have more than theoretically adequate amounts of the parent dietary EFAs, we have concluded that the risk of biliary abnormalities and gall stones is related to deficits of the 6-desaturated EFAs in such patients. Both the n-6 and the n-3 desaturated EFAs such as stearidonic acid, EPA or DHA are particularly important in preventing gall stones. This can be concluded from epidemiological investigations in Eskimos who very rarely suffer from gallstones. Eskimo plasma is unusually rich in DGLA, EPA and DHA. We therefore propose that addition of 6-desaturated n-3 EFAs, either alone or preferably in association with GLA or DGLA, will prevent the development of biliary sludging and of gall stones in patients on enteral or parenteral nutrition.

In this aspect, again within the broad statement given, the invention may be considered as:

1. A method of preventing or reversing biliary sludging and gall stones, in patients undergoing parenteral nutrition or enteral nutrition with artificial fluids, by adding 6-desaturated EFAs of the n-3 series and more particularly stearidonic acid (SA), EPA or DHA to the enteral fluid. The fatty acid is preferably added in amounts in the range of 0.01 to 20% of the dry weight of the enteral feed, more preferably 0.05 to 10% and very preferably 0.5 to 2.0%.

2. Such method in which n-6 series EFAs, particularly GLA or DGLA, are also added to the fluid preferably in the same range of concentrations as the n-3 EFAs.

3. A method of preventing or reversing biliary sludging and gall stones, in patients undergoing parenteral nutrition by applying enterally 6-desaturated EFAs of the n-3 series and more particularly SA, EPA or DHA, preferably in an amount of 0.01 to 30 g per day, more preferably 0.2 to 10 g per day and very preferably 0.5 to 3 g per day.

4. Such method in which n-6 series EFAs, particularly GLA or DGLA, are also added to the fluid, preferably in the same amounts as the n-3 EFAs.

5. A method of preparing a medicament for preventing or reversing biliary sludging and gall stones, in patients undergoing parenteral or enteral nutrition, said medicament containing 6-desaturated EFAs of the n-3 series and more particularly SA, EPA or DHA in the form of sterile ampoules or other appropriate presentations. This medicament may be added to fluids for parenteral or enteral nutrition or alternatively be given separately. Such presentations should desirably contain sufficient EFA to provide from 0.1 to 1000 mg/kg/day, preferably 1 mg to 100 mg/kg/day and very preferably 10 mg to 40 mg/kg/day.

6. Such method in which n-6 series EFAs, particularly GLA or DGLA are incorporated in addition to the n-3 EFAs and preferably in the same amounts.

Fatty Acids

The pathways of conversion of the main series of polyunsaturated fatty acids in the body are as in Table 2 below:

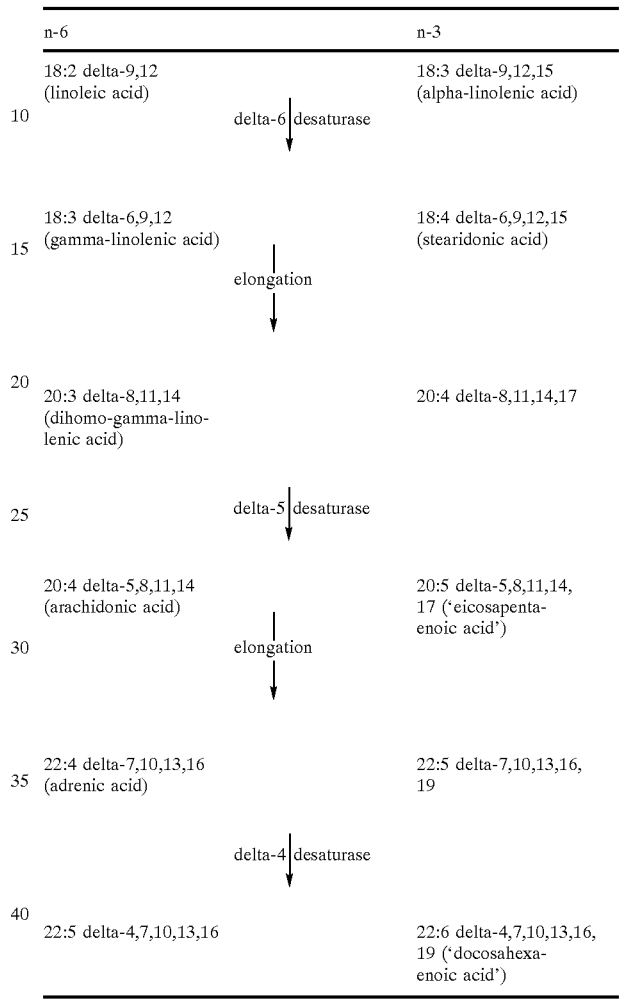

TABLE 2

As appears from the pathways, the "6-desaturated" EFAs are those whose generation in the healthy body from dietary linoleic acid and alpha-linolenic acid include a 6-desaturase step, and are the 18:3 and higher acids of the natural n-6 series and the 18:4 and higher acids of the natural n-3 series of EFAs.

The pathways are not normally reversible nor, in man, are n-3 and n-6 series acids inter-convertible.

The acids, which in nature are of the all-cis configuration, are systematically named as derivatives of the corresponding octadecanoic, eicosanoic or docosanoic acids, e.g. delta-9, 12-octadecadienoic acid or delta-4,7,10,13,16,19 docosahexaenoic acid, but numerical designations such as, correspondingly, 18:2 n-6 or 22:6 n-3 are convenient. Initials, for example, EPA for the 20:5 n-3 acid (eicosapentaenoic acid) or DHA for the 22:6 n-3 acid (docosahexaenoic acid), are also used but do not serve when n-3 and n-6 acids of the same chain length and degree of unsaturation exist as for example with the 22:5 acids. Trivial names in more or less common use in the n-6 series are as shown. Of the n-3 series only 18:3 n-3 has a commonly used trivial name, alpha-linolenic acid, though the name stearidonic acid is coming into use for the 18:4 n-3 acid and the names eicosapentaenoic acid and docosahexanenoic acid as such are also used. The alpha isomer of linolenic acid was characterised earlier than gamma-linolenic acid and reference in the literature simply to linolenic acid, especially in the earlier literature, is to the alpha-acid.

Derivatives of EFAs

As indicated above, the acids may be used as such or as pharmaceutically acceptable and physiologically equivalent derivatives as, for example, detailed below for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloro-form:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard-fatty acid methyl esters.

Forms and Sources of Gamma-Linolenic and Other Acids

Convenient physiologically equivalent derivatives of GLA and DGLA for use according to the invention as with the other acids, include salts, amides, esters including glyceride esters and alkyl (e.g. $C_1$ to $C_4$) esters, and phospholipids. In particular lithium salts may be used, when lithium will be present as ca. 2% by weight related to the fatty acids themselves, with suitable dosages related to fatty acid amounts accordingly.

If desired, pharmaceutical compositions may be produced for use in the invention by associating the natural or synthetic acids, as such or as derivatives, with an acceptable pharmaceutical vehicle. It is, however, at present convenient to provide at least GLA in the form of an available oil having a high GLA content, hence reference to "oils" herein.

One source of oils currently available is the seed of evening primrose species such as *Oenothera biennis L.* and *Oenothera lamarckiana*, the oil extract therefrom containing about 8% GLA and about 72% linoleic acid in the form of their glycerides, together with other glycerides (percentages based on total fatty acids). Other sources of GLA are borage species such as *Borago officinalis* which, though current yield per acre is low, provide a richer source than Oenothera oil. Oils from the seeds of members of the Ribes family are also often rich in GLA. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the triglycerides of gamma-linolenic and linoleic acids as the main fatty acid components, the gamma-linolenic acid content being, if desired, a major proportion. Seed oil extracts appear to have a stabilising effect upon DGLA if present.

Sources of Other N-6 Series Acids

DGLA can be prepared by chemical synthesis or by fungal fermentation. For the higher n-6 acids, natural sources of 22:4 and 22:5 n-6 acids include adrenal glands (22:5) and kidneys (22:4) obtained from slaughter houses, which also give AA sources, and 22:4 in the fat of the American Snapping Turtle. AA can also be prepared by fermentation of various types of fungi and algae.

Sources of N-3 Series Acids

The n-3 acids are available from marine oils, particularly the 20:5 n-3 and 22:6 n-3 acids, and more recently from microbial fermentation. They can be isolated from these sources by, for example, saponification under mild non-oxidising conditions followed by preparative gas liquid chromatography. Synthesis is difficult but not impossible and provides another source.

Pharmaceutical Presentation

Advantageously, a preservative is incorporated into the preparation. Alpha-tocopherol in concentration of about 0.1% by weight has been found suitable for the purpose and is one of a number of possible stabilisers well known in the field and including also for example ascorbyl palmitate and stearate. Of particular value is the antioxidant mixture developed by Scotia and described in patents.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

The following examples are formulations appropriate for prevention or reversal of complications of enteral and parenteral nutrition including intestinal atrophy or of biliary sludging and gallstones and/or of fat accumulation in the liver in patients at risk of or suffering from the same:

Examples 1 to 8

A parenteral lipid emulsion is used containing 10% to 30% total lipid by volume in a per se conventional pyrogen-free formulation. "INTRALIPID 10%" oil in water emulsion (trade mark, Kabi-Vitrum) containing per 500 ml water at pH7 is an example of such an emulsion and several other similar formulations are generally marketed.

| | | |
|---|---|---|
| Fractionated soybean oil | 50 | g |
| Fractionated egg phospholipids | 6 | g |
| Glycerol | 11 | g |

According to the invention (a) 5%, (b) 10% or (c) 15% of the lipid present in this type of emulsion, by weight, is taken up by one or other of the following mixtures of EFAs, the EFAs being provided as triglycerides, free fatty acids or ethyl esters or appropriate salts, including the lithium salt and being added to the emulsion in an appropriate way known to those skilled in the art.
The figures show the proportional composition of the added EFA or EFA mixture:

TABLE 3

| Example | GLA | DGLA | SA | EPA | DHA |
|---|---|---|---|---|---|
| 1 | 100 | — | — | — | — |
| 2 | 50 | 50 | — | — | — |
| 3 | 50 | — | 50 | — | — |
| 4 | 50 | — | — | 30 | 20 |
| 5 | — | 60 | — | 20 | 20 |
| 6 | — | 80 | 20 | — | — |
| 7 | 80 | — | — | 20 | 10 |
| 8 | — | — | — | 80 | 20 |

Examples 9 to 16
Parenteral lipid emulsions are administered as above where the total amount of lipid present is (a) 15% or (b) 20% by volume.

Examples 17 to 24
Enteral feeds, again of generally conventional formulation and selected from those given following Examples 57 to 64, are administered containing according to the invention 5% total lipid in which (a) 10%, (b) 20% or (c) 30% of that lipid by weight consists of fatty acids in the proportions in Table 3 above.

Examples 25 to 32
Enteral feeds similar to the above but in which the total lipid content is (a) 3% (b) 10%, (c) 15% or (d) 20%.

The invention is also illustrated in the following, for use in the prevention or reversal of intestinal atrophy or of fatty liver or of biliary sludging and gallstones in patients at risk of or suffering from the same:

Examples 33 to 40
Ampoules containing 20 ml of lipid in which are contained the amounts of the EFAs (mg) shown below. One ampoule to be added to the enteral or parenteral fluids being administered to a patient per day:

| Example | GLA | DGLA | SA | EPA | DHA |
|---|---|---|---|---|---|
| 33 | 1000 | — | 100 | 100 | 100 |
| 34 | — | 1000 | — | 200 | 100 |
| 35 | 2000 | — | — | 500 | — |
| 36 | 2000 | — | — | 1500 | 500 |
| 37 | 500 | 500 | 200 | 200 | — |
| 38 | — | — | — | 1000 | 500 |
| 39 | — | — | — | 750 | 750 |
| 40 | 500 | — | — | 1000 | 500 |

Examples 41 to 48
Ampoules as above in which the total amount of lipid in the ampoule is (a) 10, (b) 15 or (c) 30 ml.

Examples 49 to 56
Micro-encapsulated oil mixtures presented as a dry powder in which the oil is contained in micro-capsules of gelatin, gum arabic, agar, dextran or other appropriate material presented in sealed sachets containing (a) 20, (b) 40 or (c) 60 g of powder, of which 20 to 30% is lipid containing the amounts of fatty acids shown in Examples 33 to 40. The powder from such sachets to be mixed up with materials for enteral nutrition.

Examples 57 to 64
Examples as in 1 to 8 and 17 to 24, but in which the enteral and parenteral supplements are given together to ensure optimum delivery of the fatty acids to both surfaces of the intestine.

In all the above Examples the EFAs may be presented in purified or partially purified forms or in the form of natural vegetable or microbial or fish or other oils containing the appropriate fatty acids.
The actual enteral and parenteral feeds to which the EFAs are added are as follows:

For Examples 1 to 16, the commercial lipid emulsion to which the EFAs are added is "INTRALIPID" (trade mark, Kabi-Vitrum) as set out in Example 1. However, other similar emulsions prepared by other manufacturers may also be used.

For Examples 17 to 32, examples of enteral feeds to which the EFAs are added are "CLINIFEED" (trade mark, Roussel), "VIVONEX" (trade mark, Norwich Eaton), "ENRICH" and "ENSURE" (trade mark, Abbott), "FLEXICAL" (trade mark, Bristol-Myers), "FRESUBIN" (trade mark, Fresenius), and "LIQUISORB" (trade mark, Merck).

"CLINIFEED" contains protein (casein and soya), carbohydrate (maltodextrin, glucose), fat (corn oil, soya oil), vitamins and minerals (gluten- and lactose-free) liquid feed 375 ml × 20 1.57 MJ/tin
"VIVONEX" contains amino acids 7.7%, glucose solids 86.3%, essentiai fat 0.5%, vitamins and minerals (gluten-, lactose-, sucrose- and fructose-free) powder 1.57 MJ/100 g
"ENRICH" contains protein (casein, soya protein isolate) 4%, carbohydrate (corn syrup soilds, sucrose) 14.1%, dietary fiber (soya polysaccharides) 2.1%, fat (corn oil) 3.7%, vitamins and minerals (gluten- and lactose-free) liquid 0.46 MJ/100 ml
"ENSURE" contains protein (casein, soya protein isolate) 3.7%, carbohydrate (corn syrup solids, sucrose) 14.6%, fat (corn oil) 3.7%, vitamins and minerais (gluten- and lactose-free, electrolyte-low) liquid 0.45 MJ/100 ml
"FLEXICAL" contains protein (casein hydrolysate, amino acids) 9.9%, carbohydrates (tapioca starch, corn syrup solids) 66.9%, fat (soya oil, medium chain triglycerides) 15%, vitamins and minerals (gluten- and lactose-free) powder 1.85 MJ/100 g
"FRESUBIN" contains protein (milk and soya protein) 3.8% carbohydrate (maize starch) 13.8%, fat (sunflower oil) 3.4%, vitamins, minerals, lactose-low (0.01%) (gluten-free, eiectrolyte-low) liquid feed 0.42 MJ/100 ml
"LIQUISORB" Contains protein (lactoproteins) 4 g, carbohydrate (mono-, di-, oligo- and poly-saccharides) 11.8 g, fat (soya bean oil) 4 g per 100 ml. Vitamins, minerals and trace elements (gluten-free and lactose-low) liquid 0.42 MJ/100 ml.

For Examples 33 to 40, all the above enteral and parenteral feeds are suitable, as indeed are other similar types of feed.

We claim:

1. A method of reducing the occurrence of or preventing atrophy of the intestine in a person receiving parenteral or fluid diet enteral nutrition comprising administering gamma-linolenic acid or dihomo-gamma-linolenic acid or both in amounts of from 0.1 mg to 1 g per kg body weight per day said acid being contained in, or administered in addition to, a parenteral or fluid-diet enteral nutritional composition.

2. The method according to claim 1, wherein the acid is gamma-linolenic acid.

3. The method according to claim 1, wherein the acid is added in an amount in the range of from 0.01 to 20% of the dry weight of the enteral nutritional composition.

* * * * *